(12) United States Patent
Takagi

(10) Patent No.: US 9,194,809 B2
(45) Date of Patent: Nov. 24, 2015

(54) JIG FOR FLEXIBLE OPTICAL MEASUREMENT

(71) Applicant: Akira Takagi, Koganei (JP)

(72) Inventor: Akira Takagi, Koganei (JP)

(73) Assignees: SUMITOMO CHEMICAL COMPANY, LIMITED, Tokyo (JP); DAI NIPPON PRINTING CO., LTD., Tokyo (JP)

( * ) Notice: Subject to any disclaimer, the term of this patent is extended or adjusted under 35 U.S.C. 154(b) by 0 days.

(21) Appl. No.: 14/363,320

(22) PCT Filed: Dec. 6, 2012

(86) PCT No.: PCT/JP2012/081687
§ 371 (c)(1),
(2) Date: Jun. 6, 2014

(87) PCT Pub. No.: WO2013/089017
PCT Pub. Date: Jun. 20, 2013

(65) Prior Publication Data
US 2014/0307257 A1 Oct. 16, 2014

(30) Foreign Application Priority Data

Dec. 16, 2011 (JP) .................................. 2011-007435
Dec. 4, 2012 (JP) .................................. 2012-265186

(51) Int. Cl.
| | | |
|---|---|---|
| *G01N 21/01* | (2006.01) | |
| *G01N 21/84* | (2006.01) | |
| *G02F 1/13* | (2006.01) | |
| *G01B 5/00* | (2006.01) | |
| *G02F 1/1333* | (2006.01) | |

(52) U.S. Cl.
CPC .............. *G01N 21/84* (2013.01); *G01B 5/0004* (2013.01); *G01N 21/01* (2013.01); *G02F 1/1309* (2013.01); *G02F 1/133305* (2013.01)

(58) Field of Classification Search
CPC ............. G01N 31/229; G02B 19/0019; G02B 19/0042; G02B 1/105; G02B 26/0816; G02B 5/08; G02B 5/0808; G02B 5/10; G02B 5/282; G02B 7/183
See application file for complete search history.

(56) References Cited

U.S. PATENT DOCUMENTS

| | | | | |
|---|---|---|---|---|
| 4,563,088 A | * | 1/1986 | Gullman | 356/244 |
| 5,343,288 A | * | 8/1994 | Cohen et al. | 356/239.1 |
| 5,574,554 A | * | 11/1996 | Su et al. | 356/124 |
| 5,781,288 A | * | 7/1998 | Asakura et al. | 356/239.1 |
| 6,314,199 B1 | * | 11/2001 | Hofer et al. | 382/141 |
| 7,556,554 B2 | * | 7/2009 | Brug et al. | 451/2 |

FOREIGN PATENT DOCUMENTS

| | | |
|---|---|---|
| JP | 2008-058274 A | 3/2008 |
| JP | 2010-91509 A | 4/2010 |
| JP | 2010-127910 A | 6/2010 |

OTHER PUBLICATIONS

Form PCT/ISA/210 International Search Report issued in International Application No. PCT/JP2012/081687 with English translation, date of mailing Mar. 26, 2013 (4 pages).

* cited by examiner

*Primary Examiner* — Michael P Stafira
(74) *Attorney, Agent, or Firm* — Flynn, Thiel, Boutell & Tanis, P.C.

(57) ABSTRACT

A jig for flexible optical measurement has a holding member which has a prescribed curvature that allows it to hold a flexible optical display panel with any given curvature, and a base member which has the same curvature as the holding member in order to shift the holding member and is used to shift the holding member. The holding member can be shifted using the base member, and when performing any measurement by shifting the flexible optical display panel and measuring, it is possible to measure the measurement position from the normal direction.

3 Claims, 7 Drawing Sheets

(a)

(b)

JIG FOR FLEXIBLE OPTICAL MEASUREMENT

TECHNICAL FIELD

The present invention relates to a jig for flexible optical measurement which makes it possible to measure optical characteristics of a flexible optical display panel with an arbitrary curvature.

BACKGROUND ART

Recently, digital signage has been attracting attention, and flexible optical display panels that can be placed in any shape are being developed. It is necessary to measure optical characteristics of these flexible optical display panels. Conventionally, optical characteristics of a display part of a display device are measured by measuring physical quantities such as luminance and chromaticity of the display part in the manufacturing process of the display device (Patent Literature 1).

CITATION LIST

Patent Literature

Patent Literature 1: JP 2010-91509 A

SUMMARY OF INVENTION

Technical Problem

However, conventional optical measurement devices have structures designed on the assumption of measuring flat panels. Accordingly, when a flexible optical display panel is measured in a bent state, such problems occur that the focal point differs between an end portion and the middle portion to cause changes in the diameter of the measuring light spot, and that the display panel has to be evaluated from an oblique direction with respect to a plane to be measured. Consequently, accurate measured values cannot be obtained.

The present invention has been made considering these situations, and aims at providing a jig for flexible optical measurement that makes it possible, in any measurement of a flexible optical display panel with an arbitrary curvature, to perform measurement always from a normal direction to a measurement position.

Solution to Problem

To solve the above-described problems and to achieve the above-mentioned aim, the present invention is configured as follows.

An invention (1) is a jig for flexible optical measurement, including: a holding member having such a specified curvature that can hold a flexible optical display panel with an arbitrary curvature; and a base member for allowing the holding member to move and having the same curvature as that of the holding member to allow the holding member to move, wherein the holding member is movable by the base member so that measurement is possible from a normal direction to a measurement position in any measurement in which the flexible optical display panel is moved and measured.

An invention (2) is the jig for flexible optical measurement according to (1), wherein the holding member is a plate-like member having a surface with a specified curvature, and includes: a holding portion capable of holding the flexible optical display panel on the surface with the specified curvature; an opening formed on the holding portion to perform optical measurement; and slide portions provided at both ends of the holding portion to allow the holding portion to move relative to the base member.

An invention (3) is the jig for flexible optical measurement according to (1), wherein the base member includes: a base portion to enable the base member to be placed; an opening formed on the base portion to perform optical measurement; and a guide portion provided on the base portion to allow the holding member to move.

An invention (4) is the jig for flexible optical measurement according to (1), wherein the base member includes: a scale that indicates a moving amount of the holding member; and a measurement mark that indicates a measurement position of the flexible optical display panel.

An invention (5) is the jig for flexible optical measurement according to (1), wherein the base member includes a fastening member that fastens the holding member to fix the flexible optical display panel in a measurement position.

Advantageous Effects Of Invention

With the configurations as described above, the present invention has the following advantageous effects.

According to the invention as described in each of (1) to (5), the base member has the same curvature as that of the holding member, and allows the holding member to move. Since the holding member is allowed to move by the base member, in any measurement in which a flexible optical display panel is moved and measured, it is possible to perform measurement from a normal direction to a measurement position. Accordingly, accurate measured values can be obtained without causing such problems that the focal point changes to cause changes in the diameter of the measuring light spot and that the display panel is evaluated from an oblique direction with respect to a plane to be measured. As a result, flexible optical display panels can be evaluated accurately.

DESCRIPTION OF EMBODIMENTS

Hereinafter, an embodiment of a jig for flexible optical measurement of the present invention will be described. It should be understood that this embodiment is a best mode of the present invention, and that the present invention is not limited to this embodiment.

(Structure of a Jig for Flexible Optical Measurement)

Figure 1:
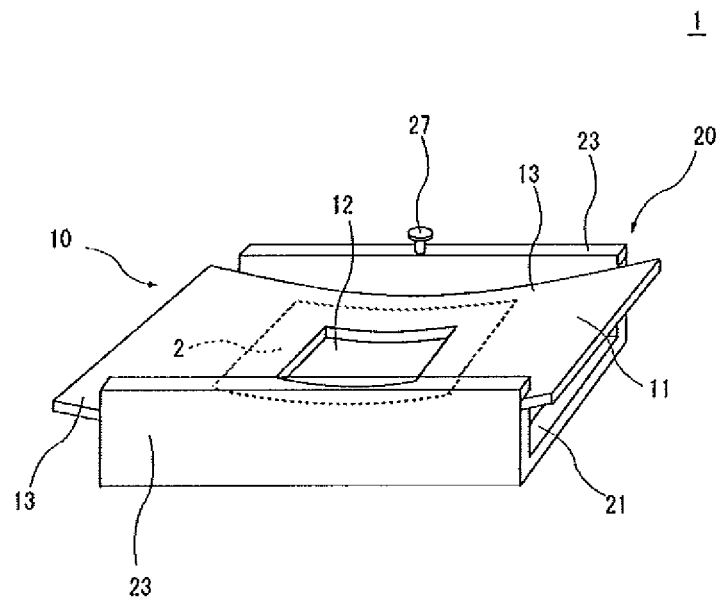
FIG. 1 is a perspective view of a jig for flexible optical measurement.
Figure 2:
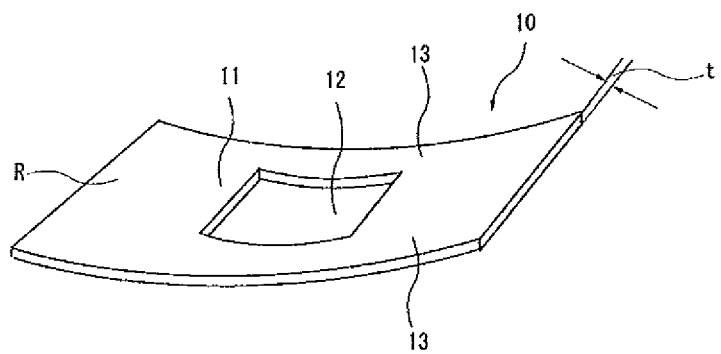
FIG. 2 is a perspective view of a holding member.
Figure 3:
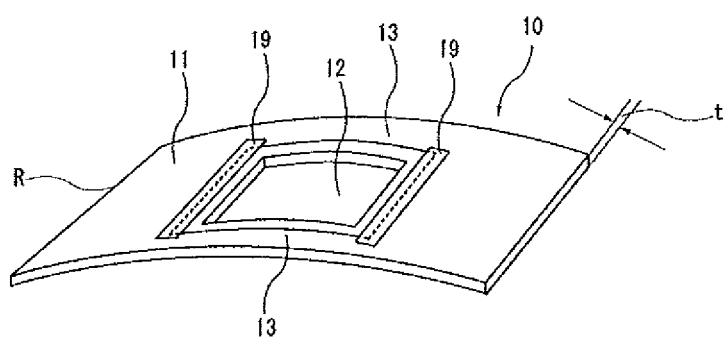
FIG. 3 is a perspective view showing a state in which a flexible optical display panel is fixed to the holding member.

FIG. 1 is a perspective view of a jig for flexible optical measurement. FIG. 2 is a perspective view of a holding member. FIG. 3 is a perspective view showing a state in which a flexible optical display panel is fixed to the holding member.

Figure 4:
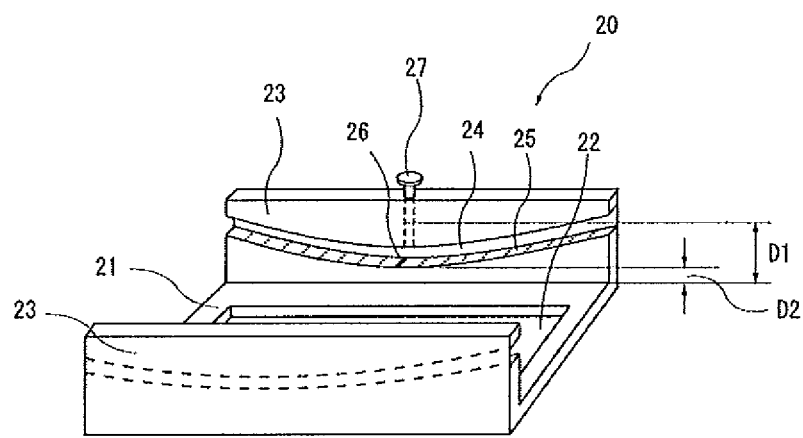
FIG. 4 is a perspective view of a base member.
Figure 5:
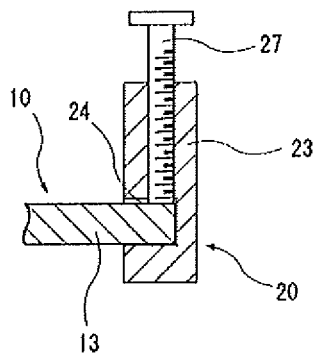
FIGS. 5(a) and 5(b) are sectional views each showing a position of allocating a fastening member.
Figure 5:
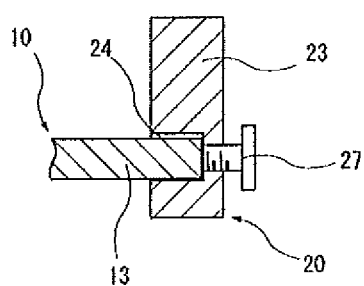

FIG. 4 is a perspective view of a base member. FIGS. 5(a) and 5(b) are sectional views each showing a position of allocating a fastening member.

A jig for flexible optical measurement 1 of this embodiment is used in a process of manufacturing a flexible optical display panel 2 to measure optical characteristics of a display portion of the flexible optical display panel 2 such as luminance, chromaticity and cell gap. This jig for flexible optical measurement 1 is configured by a holding member 10 having such a specified curvature that can hold a flexible optical display panel 2 with an arbitrary curvature, and a base member 20 for allowing the holding member 10 to move and having the same curvature as that of the holding member 10 to allow the holding member 10 to move. The holding member 10 is movable by the base member 20 so that measurement is possible from a normal direction to a measurement position in any measurement of the flexible optical display panel 2.

The holding member 10 is a plate-like member having a surface with a specified curvature. The holding member 10 has a holding portion 11 capable of holding the flexible optical display panel 2 on the surface with the specified curvature, an opening 12 formed on the holding portion 11 to perform optical measurement, and slide portions 13 at both ends of the holding portion 11 to allow the holding portion 11 to move relative to the base member 20.

The holding member 10 has a thickness t and a radius of curvature R, and fixes the flexible optical display panel 2 on the convex surface with the radius of curvature R of the holding portion 11. The flexible optical display panel 2 may be fixed so as not to affect the display area of the flexible optical display panel 2 and so as to prevent the flexible optical display panel 2 and the holding member 10 from shifting in position from each other during handling.

For example, the fixing method may be a method in which the holding member 10 and the flexible optical display panel 2 are provided with screw holes and fastened by fastening means, a method in which the outer periphery or only an end in the bent direction of the flexible optical display panel 2 is fixed with a metal fitting or a plastic plate, or a method in which the flexible optical display panel 2 is simply adhered to the holding member 10 with a strong adhesive tape. Although the flexible optical display panel 2 is fixed with a strong adhesive tape 19 in this embodiment, the fixing method used in the present invention is not limited to this method.

The holding member 10 includes one or plural openings 12 on the holding portion 11. The size of each opening and the number of the openings 12 may be determined depending on the measuring light spot diameter and the measurement position of the flexible optical display panel 2, and thus may be arbitrary.

The base member 20 includes a base portion 21 to enable the base member to be placed, an opening 22 formed on the base portion to perform optical measurement, and guide portions 23 provided on the base portion 21 to allow the holding member 10 to move. At the guide portions 23, guide grooves 24 are provided to allow the slide portions 13 of the holding member 10 to be movable. Each of the guide grooves 24 has the same radius of curvature R as that of the holding member 10 to allow the support portions 13 of the holding member 10 to be movable.

Each of the guide portions 23 of the base member 20 has a scale 25 that indicates a moving amount of the holding member 10, and a measurement mark 26 that indicates a measurement position of the flexible optical display panel 2. Since the scale 25 and the measurement mark 26 are formed on the guide grooves 24 of the guide portions 23, the holding member 10 is molded by a transparent resin. However, when the scale 25 and the measurement mark 26 are formed on the side surfaces of the guide portions 23 along the guide grooves 24, the holding member 10 may not be limited to a transparent resin. In the manner as described above, the scale 25 and the measurement mark 26 are formed so as to be easily visible from the outside.

Also, the base member 20 includes a fastening member 27 that fastens the holding member 10 to fix the flexible optical display panel 2 in the measurement position. The fastening member 27 is formed by a fastening screw, and may have either a structure in which the fastening screw fastens to fix an end portion on the front surface of the holding member 10 located in a guide groove 24 from the upper end of a guide portion 23 as shown in FIG. 5(a) or a structure in which the fastening screw fastens to fix a side surface of the holding member 10 located in the guide groove 24 from the outside of the guide portion 23 as shown in FIG. 5(b).

The base member 20 may have a size determined to a certain extent depending on the size of the holding member 10, but it may not necessarily be formed to be in proportion to the size of the holding member 10. The base member 20 includes the fastening member 27 to fix the holding member 10 to the base member 20, so that the measurement can be adequately performed by fastening the fastening member 27 in the measurement position of the flexible optical display panel 2.

The measurement mark 26 is at the lowest position D2 of the height D1 of each of the guide grooves 24. Further, each of the guide portions 23 includes the scale 25 made of marks put at constant intervals on the surface with the radius of curvature R. By matching the measurement mark 26 with a position desired to be measured of the flexible optical display panel 2 and moving the holding member 10, it is possible to perform measurement from the normal direction to the measurement position in any measurement.

Also, the scale 25 indicates a moving amount of the holding member 10. Accordingly, it is possible to change the measurement position of the flexible optical display panel 2 by moving the holding member 10 based on the scale 25. By using the scale 25, reproducibility of repeated measurements is improved.

(Optical Measurement using the Jig for Flexible Optical Measurement)

Figure 6:
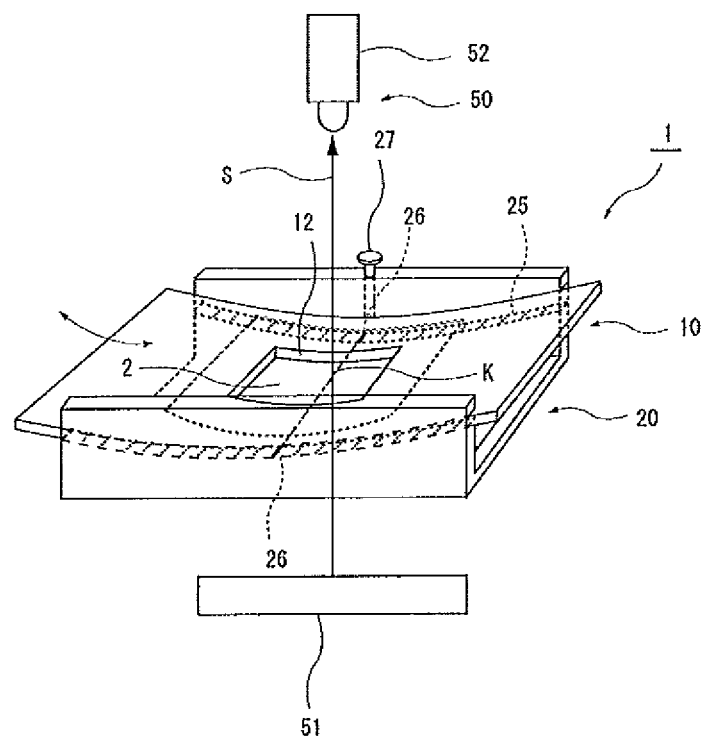
FIG. 6 is a diagram showing a positional relation of a jig for flexible optical measurement and an optical measurement device during measurement.

Next, an optical measurement using the jig for flexible optical measurement will be described based on FIG. 6. FIG. 6 is a diagram showing a positional relation between the jig for flexible optical measurement and an optical measurement device during measurement.

This optical measurement device 50 includes a light emitting unit 51 and a light receiving unit 52, and is used in a process of manufacturing the flexible optical display panel 2 to measure the optical characteristics of the display portion of the flexible optical display panel 2 by measuring the physical quantity of such as luminance and chromaticity of the display portion of the flexible optical display panel 2. The measurement of the optical characteristics is performed by applying a light from the light emitting unit 51 to the display portion of the flexible optical display panel 2, and receiving a light by the light receiving unit 52.

To perform a measurement using the optical measurement device 50, the jig for flexible optical measurement 1 is set on a light ray S so that a line K connecting the measurement marks 26 on the opposing guide portions 23 matches with a portion to be measured of the flexible optical display panel 2. The position of the flexible optical display panel 2 located at the intersection of the light ray S of the optical measurement device 50 and the line K corresponds to a position at which the flexible optical display panel 2 is measured from a normal direction to a portion to be measured. In this measurement of optical characteristics, measurement from the normal direction to the measurement position is made possible in any measurement by moving the holding member 10 of the jig for flexible optical measurement 1 by the base member 20. The flexible optical display panel 2 is moved in such a manner that the holding member 10 is moved based on the scale 25 to change the measurement position of the flexible optical display panel 2.

Figure 7:
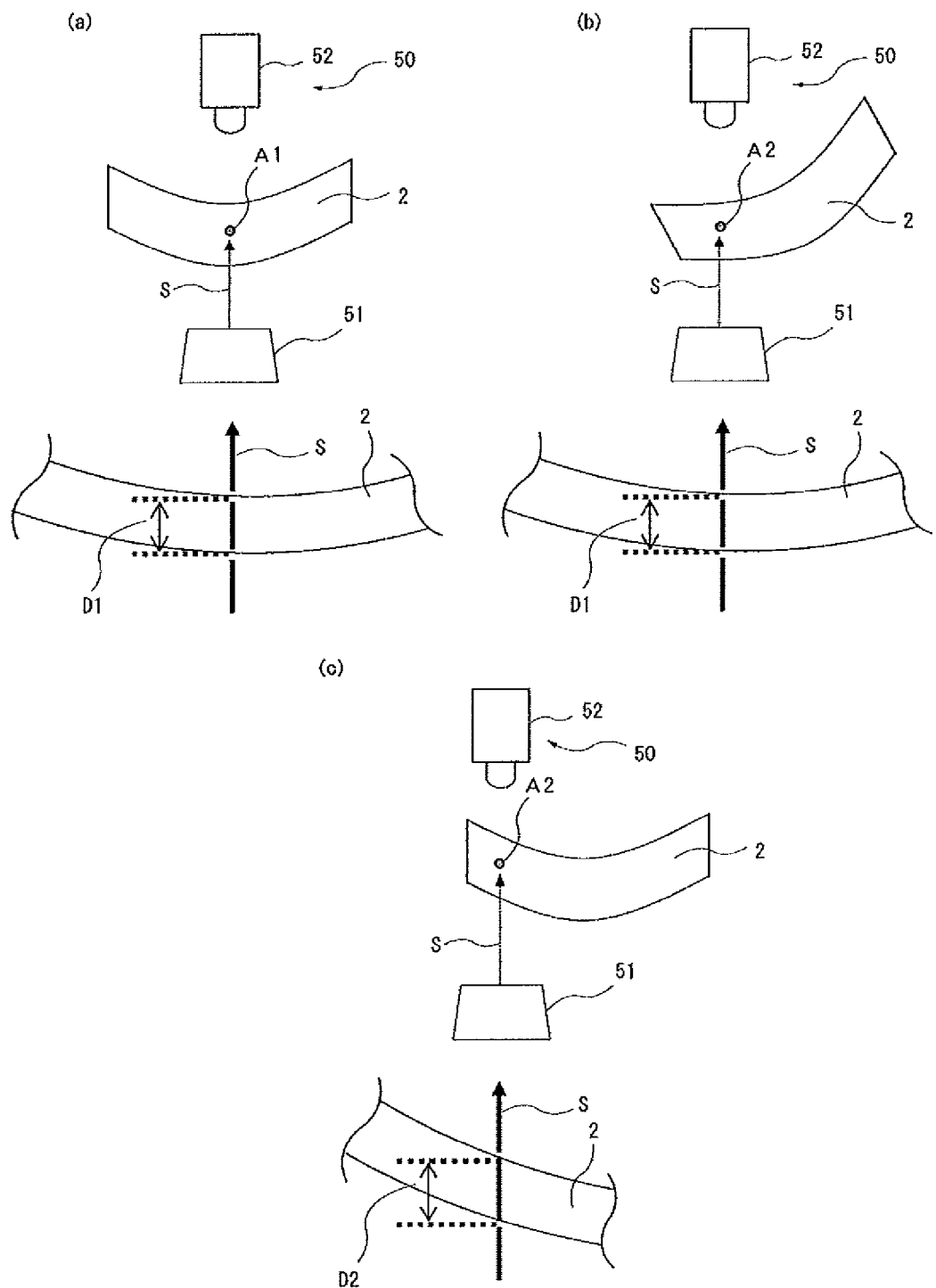
FIGS. 7(a) to 7(c) are conceptual diagrams of optical measurement.

As shown in conceptual diagrams of optical measurement in FIGS. 7(a) to 7(c), according to this embodiment, optical measurement of a flexible optical display panel 2 with an arbitrary curvature is performed by the optical measurement device 50 by using the jig for flexible optical measurement 1. This optical measurement device 50 performs measurement by matching the normal direction at a measurement point A1 of the flexible optical display panel 2 with the light ray S of the optical measurement device 50 (FIG. 7(a)). In this state, the thickness of the flexible optical display panel 2 at the measurement point A1 is D1, which is the thickness in the normal direction matched with the light ray S. In order to change the measurement position of the flexible optical display panel 2, the flexible optical display panel 2 is moved by the jig for flexible optical measurement 1 to perform measurement at a measurement point A2 (FIG. 7(b)). At this measurement point A2 also, the normal direction of the flexible optical display panel 2 matches with the light ray S of the optical measurement device 50, so that the thickness of the flexible optical display panel 2 is D1, which is the thickness in the normal direction. As described above, in any measurement in which the measurement position of the flexible optical display panel 2 is changed, the thickness of the flexible optical display panel 2 at any measurement point is always the thickness D1 in the normal direction, so that a measurement portion of the flexible optical display panel 2 can be evaluated from the normal direction.

In the comparative example in which the jig for flexible optical measurement 1 is not used, measurement is performed without matching the normal direction at the measurement point A2 of the flexible optical display panel 2 with the light ray S of the optical measurement device 50. In this case, the thickness of the flexible optical display panel 2 at the measurement point A2 becomes D2 longer than D1. As described above, in the comparative example, in which measurement is performed without using the jig for optical flexible measurement 1, measurement must be performed under the condition that the thickness is shifted from that in the normal direction.

As described above, according to this embodiment, in any measurement in which the measurement position of the flexible optical display panel 2 with an arbitrary curvature is changed, measurement is performed from the normal direction to the flexible optical display panel 2. Accordingly, accurate measured values can be obtained without causing such problems that the focal point changes to cause changes in the diameter of the measuring light spot, and that the display panel is evaluated from an oblique direction with respect to a plane to be measured. As a result, the flexible optical display panel can be evaluated accurately.

In case of measuring a voltage-transmittance, for example, a specified voltage is applied to the flexible optical display panel 2, and a luminance at that time is measured. Unless the measurement is performed from the normal direction to the flexible optical display panel 2, the distance the light ray passes through the flexible optical display panel 2 becomes longer, so that accurate values of luminance cannot be obtained.

Also, in case of measuring the cell gap, for example, the cell gap can be measured by applying a linearly-polarized specific light ray to the flexible optical display panel 2, and measuring changes in the phase. Unless the measurement is performed from the normal direction to the flexible optical display panel 2, the distance the light ray passes through the flexible optical display panel 2 becomes longer, so that the changes in the phase cannot accurately be measured.

Also, since the holding member 10 of the jig for flexible optical measurement 1 has a certain curvature, it is possible to bend the flexible optical display panel 2 uniformly by simply placing it along the holding member 10. Also, when the holding member 10 is made of a material having a high resistance to heat and a high resistance to humidity, the flexible optical display panel 2 can be put into a reliability test in the state being fixed to the holding member 10, so that the characteristics of the curved-surface flexible optical display panel 2 can be easily evaluated. Further, the jig for flexible optical measurement 1 can be installed either transversely or vertically, so that it can be mounted to various types of optical measurement devices.

INDUSTRIAL APPLICABILITY

The present invention is applicable to a jig for flexible optical measurement that can measure optical characteristics of a flexible optical display panel with an arbitrary curvature, and makes it possible, in any measurement position of the flexible optical display panel with an arbitrary curvature, to always perform measurement from a normal direction to a measurement position.

REFERENCE SIGNS LIST 1 jig for flexible optical measurement
2 flexible optical display panel
10 holding member
11 holding portion
12 opening
13 slide portion
20 base member
21 base portion
22 opening
23 guide portion
24 guide groove
25 scale
26 measurement mark
27 fastening member

The invention claimed is:
1. A jig for flexible optical measurement, comprising:
a holding member having a curvature and holding a flexible optical display panel with an arbitrary curvature; and
a base member for allowing the holding member to move and having the same curvature as that of the holding member to allow the holding member to move,
wherein the holding member is a rectangular plate member having a surface with a specified curvature, and comprises a holding portion for holding the flexible optical display panel on the rectangular plate surface with the specified curvature, an opening formed on the holding portion to perform optical measurement and slide portions provided at both ends of the holding portion to enable the holding portion to move, the base member comprises a base portion for enabling the bass member to be placed, an opening formed on the base portion to perform optical measurement and a guide portion provided on the base portion for allowing the slide portions of the holding member to move, the flexible optical display panel is positioned in the opening of the holding member for allowing the flexible optical display panel to be held on the rectangular plate surface with the specified curvature, the curvature of the flexible optical display panel is matched with the curvature of the holding member and optical measurement of a measurement position of the flexible optical display panel is made possible from a normal direction in any measurement in which the flexible optical display panel is moved and optically measured according to the movement of the holding member resulting from moving the holding member along the curvature of the base member by means of the slide portions of the holding member and the guide portion of the base member.

2. The jig for flexible optical measurement according to claim 1, wherein the base member includes:
- a scale that indicates a moving amount of the holding member; and
- a measurement mark that indicates a measurement position of the flexible optical display panel.

3. The jig for flexible optical measurement according to claim 1, wherein the base member includes a fastening member that fastens the holding member to fix the flexible optical display panel in a measurement position.

* * * * *